US007846419B2

(12) United States Patent
Fritzler et al.

(10) Patent No.: US 7,846,419 B2

(45) Date of Patent: Dec. 7, 2010

(54) METHOD FOR PRODUCING RADIOACTIVE ISOTOPES FOR POSITRON EMISSION TOMOGRAPHY

(75) Inventors: Sven Fritzler, Erlangen (DE); Peter Schardt, Höchstadt (DE); Stefan Setzer, Rudolstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1192 days.

(21) Appl. No.: 11/638,905

(22) Filed: Dec. 14, 2006

(65) Prior Publication Data

US 2007/0273308 A1 Nov. 29, 2007

(30) Foreign Application Priority Data

Dec. 22, 2005 (DE) ....................... 10 2005 061 560

(51) Int. Cl.
*A61K 51/00* (2006.01)
*A61M 36/14* (2006.01)

(52) U.S. Cl. .................... 424/1.81; 424/1.11; 424/1.85; 424/1.89

(58) Field of Classification Search ................ 424/1.11, 424/1.65, 1.81, 1.85, 1.89, 9.1, 9.4
See application file for complete search history.

(56) References Cited

U.S. PATENT DOCUMENTS

| | | | |
|---|---|---|---|
| 4,812,775 | A | 3/1989 | Klinkowstein et al. |
| 5,037,602 | A | 8/1991 | Dabiri et al. |
| 6,011,825 | A | 1/2000 | Welch et al. |
| 2004/0013219 | A1 | 1/2004 | Wieland et al. |
| 2005/0242276 | A1 | 11/2005 | Okazaki et al. |

FOREIGN PATENT DOCUMENTS

| | | | |
|---|---|---|---|
| WO | WO 01/87235 | A2 | 11/2001 |
| WO | WO 03/081604 | A1 | 10/2003 |

OTHER PUBLICATIONS

Hattori et al (Nuclear Instruments and Methods in Physics Research Section B, 1995, vol. 99, pp. 807-809).*
Volkovitsky et al, Nuclear Instruments and Methods in Physics Research Section A, 2005, vol. 548, pp. 571-573.*

* cited by examiner

*Primary Examiner*—D L Jones
(74) *Attorney, Agent, or Firm*—Brinks, Hofer, Gilson & Lione

(57) ABSTRACT

A method for producing radioactive isotopes for positron emission tomography is provided. The method includes generating radioactive isotopes by the acceleration of a projectile in a linear accelerator that is operative to accelerate at least two different projectiles.

15 Claims, 1 Drawing Sheet

METHOD FOR PRODUCING RADIOACTIVE ISOTOPES FOR POSITRON EMISSION TOMOGRAPHY

The present patent document claims the benefit of the filing date of DE 10 2005 061 560.0, filed Dec. 22, 2005, which is hereby incorporated by reference.

BACKGROUND

The present embodiments relate to a procedure for producing radioactive isotopes for positron emission tomography.

Positron emission tomography (PET) is a nuclear medicine procedure in which the distribution of a radioactively marked substance is displayed. Generally, a PET procedure uses isotopes generated with cyclotrons. For isotope generation, various nuclear reactions are used. The most important reaction is the production of $^{18}F$ by way of the reaction $^{18}O(p,n)^{18}F$.

As a result of the (p,n) reactions, neutron flows of up to $10^{11}$ neutrons per second are generated. These neutron flows necessitate considerable expense because of radiation protection needed. In conventional cyclotrons, for example, even behind the radiation protection arrangement, dosage rates of over 100 μSv/h are often reached.

Unless a major expenditure of time is tolerable, the cyclotron is generally set up for one projectile, for example, one type of particle to be accelerated, because of the adaptation made between the high frequency and the given fixed geometry. A cyclotron is generally used to generate PET isotopes. The typical weight of a cyclotron is over 50 t and has a surface area of 6 $m^2$. Cyclotrons are difficult to install because of the size and weight requirements, and the structural requirements of the cyclotron are demanding. To make the cyclotron subsequently accessible to maintenance work and repairs, a total room size of at least 50 $m^2$ for the cyclotron is necessary.

Installing a cyclotron in hospitals and examination equipment is very complicated and expensive, and an area-covering installation of cyclotrons is hardly feasible. Nuclear medicine clinics are generally supplied, for example, externally via distribution centers, with radiopharmaceuticals and biomarkers that are needed for positron emission tomography (PET).

In such external distribution centers, radiopharmaceuticals and biomarkers are as a rule produced in the morning and then sent to the hospitals. Delivery from the external distribution centers takes a certain amount of time. Accordingly, only radiopharmaceuticals or biomarkers with long-lived isotopes are sold. One suitable long-lived isotrope is, for example, the $^{18}F$-doped radiopharmaceuticals. The $^{18}F$-doped radiopharmaceuticals, whose half-life, which is 110 minutes, is comparatively long. The distribution of $^{11}C$- and $^{13}N$-doped radiopharmaceuticals via distribution centers is not done, because of the short half-lives of 20 and 10 minutes, respectively. However, $^{11}C$ radiopharmaceuticals are required for producing specific radiopharmaceuticals and biomarkers that are needed for molecular imaging. Other problems arise from the sale of $^{18}F$-doped glucose (known as FDG, for $^{18}F$-fluorodeoxyglucose). The distribution of $^{18}F$-doped glucose is limited to established radiopharmaceuticals and/or biomarkers that have been clinically evaluated. The distribution is limited because of existing regulations. However, established radiopharmaceuticals and/or biomarkers may not detect early signs of tumors.

Specific examinations in nuclear medicine are subject to narrow limits. Early and specific detection of tumors may be possible with radioactive isotopes. Therefore, it is presently desired that the production of the radioactive isotopes is more flexible and less expense.

SUMMARY

The present embodiments may obviate one or more of the limitations of the related art. For example, in one embodiment, the generation of the radioactive isotopes is lighter and requires less space than the related art.

In one embodiment, the radioactive isotopes are generated by the acceleration of a desired projectile in a linear accelerator. The linear accelerator is embodied to accelerate at least two different projectiles. The ratio of mass to charge (m/Q ratio) of the projectiles optionally differs.

In one embodiment, a linear accelerator, which is lighter in weight and smaller than a cyclotron, is used to produce the radioactive isotopes for radiopharmaceuticals and biomarkers for use in positron emission tomography (PET). The linear accelerator is light in weight and compact in size. For example, the linear accelerator has a substantially smaller mass than the cyclotrons used previously and requires substantially less space. In one embodiment, the linear accelerator is lighter in weight than a cyclotron used previously by a factor of at least 5. The space required may be reduced to a fraction of what was needed before. Accordingly, the radioisotopes may be generated more economically.

In one embodiment, the production of radioactive PET isotopes is flexible because whichever projectile is desired for the acceleration, it can be selected from a plurality of available projectiles with different mass to charge ratios. For example, different radioisotopes may be generated with different fundamental nuclear reactions, depending on the target selected, or which of at least two available projectiles is accelerated.

In one embodiment, for a skillful selection of nuclear reactions, the linear accelerator has a smaller footprint, lighter weight, and/or less radiation protection expense than the cyclotron. In this embodiment, the radioactive isotopes for PET may be generated with more flexibility and adapted to what is needed, for example, for a specific examination. The structural provisions for installing the linear accelerators may also be reduced, compared to cyclotrons.

In one embodiment, protons and/or deuterons may be used as the projectile. The use of these different types of particles increases the flexibility. For example, the use of different types of particles makes it possible, in a targeted way, to select the desired nuclear reactions that make it possible to produce radiopharmaceuticals and biomarkers that are optimally suited for a specific task in molecular imaging, or for early tumor detection. The projectiles are not limited to protons and/or deuterons. Any suitable projectile may be used for producing the PET isotopes.

In one embodiment, radioactive isotopes with half-lives of any length may be generated. In one embodiment, radioactive isotopes with half-lives of over one hour, for example, $^{18}F$, may be generated. Any suitable length may be generated, for example, $^{11}C$ and/or $^{13}N$. For example, radioactive isotopes with half-lives over and/or equal to and/or less than one hour may be generated. The half-life of $^{18}F$ is 110 minutes, the half-life of $^{11}C$ is 20 minutes, and that of $^{13}N$ is 10 minutes. The isotope generation is thus not limited to long-lived radioisotopes and corresponding radiopharmaceuticals and/or biomarkers. In one embodiment, it is additionally or alternatively possible to produce short-lived isotopes, for example, the aforementioned $^{11}C$ and $^{13}N$, and to use them for positron emission tomography (PET) in order to resolve specific questions in conjunction with functional imaging.

In one embodiment, nuclear reactions that generate alpha particles may be used. In this embodiment, high neutron flows, which occur in the generation of radioactive isotopes with the typical nuclear reactions in cyclotrons, are avoided. The required radiation protection expense is reduced as a result. In one embodiment, generation of neutrons, if any, in nuclear reactions is based on the emission of alpha particles and involves a neutron generation due to contamination of various targets. Avoiding neutron-generating nuclear reactions in favor of reactions in which alpha particles are released permits a marked reduction in radiation protection provisions and a further drop in the incident costs.

In one embodiment, the nuclear reactions $^{20}Ne(d,\alpha)^{18}F$ and/or $^{14}N(p,\alpha)^{11}C$ and/or $^{16}O(p,\alpha)^{13}N$ may be used. The neon, nitrogen, or oxygen targets are bombarded with protons or deuterons, so that the isotopes $^{18}F$, $^{11}C$, and $^{13}N$, respectively, are created. In the example nuclear reactions indicated solely alpha particles are released. The nuclear reactions are not limited to those described herein. Any suitable nuclear reaction may be used. The neutron flows that occur from contamination in the targets are extremely slight. It is comparatively simple to shield against these slight neutron flows.

In one embodiment, the radioactive isotopes are generated in a hospital and/or a clinical or diagnostic device and are used to produce radiopharmaceuticals and/or biomarkers that are needed there. In contrast to the generation of biomarkers and radiopharmaceuticals in distribution centers, the acceleration of the projectiles with the ensuing isotope production and processing into radiopharmaceuticals and/or biomarkers are done directly on-site, for example, in a hospital with a nuclear medicine department, in a clinical complex, or in a specific diagnostic center.

For example, an examination device that is specialized for tumor detection may produce its specialized radiopharmaceuticals and/or biomarkers directly and at the time they are needed. Accordingly, the examination device is not subject to fluctuations in distribution or limited to long-lived radioisotopes.

In one embodiment, a small, lightweight linear accelerator of compact construction may be used, in which the requirements for radiation protection are reduced compared to the cyclotron. In one embodiment, a linear accelerator that is designed for operation of protons and deuterons is used. In this embodiment, the system is readily predictable, so that the risk of the investment to the hospital involved may still be calculated. Unlike cyclotrons for generating PET isotopes, when linear accelerators are used to produce radioactive isotopes and radiopharmaceuticals and/or biomarkers on-site in the hospital or clinic, no separate monitoring area is needed. In this embodiment, radioisotopes are generated without major problems even with limited space available. It is understood, however, for safety reasons that access control is necessary, when the high frequency emitters on the linear accelerator are on.

In one embodiment, radioactive isotopes may be produced as needed in the desired quantity and/or type and/or with the desired projectile. The radioisotopes and the radiopharmaceuticals or biomarkers produced from them are accordingly produced "on demand" at the correct time, in the desired quantity, and of the desired type. In this embodiment, unnecessary examinations of patients with lesser specificity, for example, where diagnostic conclusiveness is limited, resulting from a limitation to a specific radioisotope that is available, are avoided.

In one embodiment, the radiopharmaceuticals and biomarkers may be adapted especially to the needs of the particular device or examination, so as to obtain optimal findings without being limited to the selection offered by a distribution center. The quantity of radioisotopes produced is also dictated only by the requirements made in the clinic, for example, without having to take shipping specifications of a distribution center or the like into account. In one embodiment, radiopharmaceuticals and/or biomarkers for positron emission tomography may be used in a more accessible and specific way with predictable costs and a reasonable amount of space.

In one embodiment, to use a different projectile, the type of gas in the source of the linear accelerator, the parameter set of the linear accelerator, and the high-frequency amplitude and the high-frequency phase are changed. In this embodiment, merely replacing the gas in the source and changing the parameters required for operation and the high frequency, a reset to whatever different type of particle is involved may be done in a very short time.

In one embodiment, projectile energies at the target of the linear accelerator may be attained. For example, the projectile energies for protons amount to about 5 MeV to 15 MeV and/or the projectile energies for deuterons amount to about 10 MeV to 20 MeV. In one embodiment, both protons and deuterons are accelerated. In this embodiment, the projectile energies at the target, for both types of particle, are restricted to the indicated range.

In one embodiment, a linear accelerator includes a radiofrequency quadrupole and an acceleration resonator operated in the H mode. In one embodiment, an acceleration resonator operated in the interdigital or the crossbar H mode, may be used, in which the beam losses in the RFQ amount to 10% or less and/or in the IH tank or the CH tank amount to 1% or less. The radiation losses in the first portion downstream of the source, in the RFQ, are accordingly ideally less than 10%. The radiation losses in the second portion downstream of the source, for example, in the IH tank or CH tank, are as much as possible less than about 1%. An effective radiation protection is thus achieved. The term "CH tank" stands for crossbar H tank. In contrast to the IH, in which the rods, at which the high frequency are carried, come from above and below in alternation, in the CH, the rods all pass through from one side, for example as crossbars.

DETAILED DESCRIPTION

Figure 1:
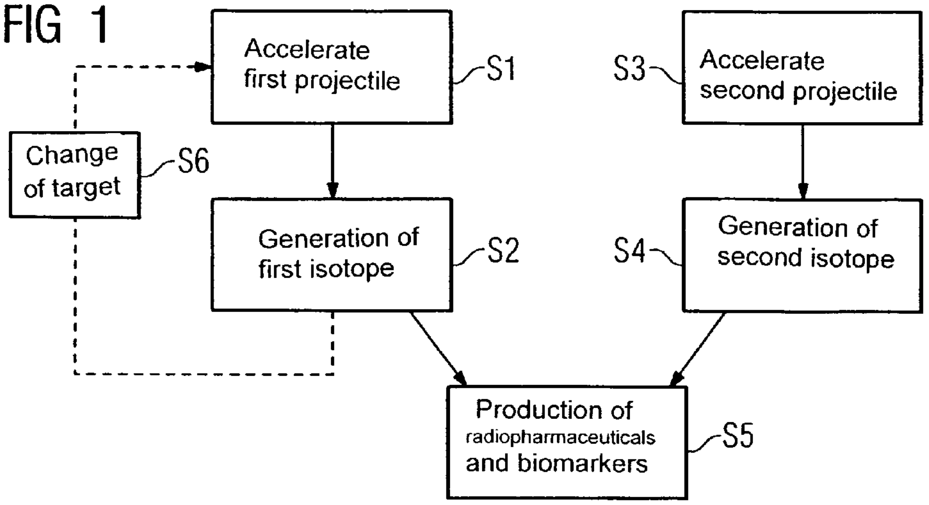
FIG. 1 is a flow chart of one embodiment of a procedure for producing radioactive isotopes for positron emission tomography.

In one embodiment, as shown in FIG. 1, a first projectile, for example, a proton projectile, is accelerated in the linear accelerator (S1). The projectile is emitted at a target, generating a first radioactive isotope (S2). In one exemplary embodiment, a carbon isotope $^{11}C$ is generated when a nitrogen target is used with the proton projectile, via the nuclear reaction $^{14}N(p,\alpha)^{11}C$. Radiopharmaceuticals and biomarkers for performing a PET examination are produced (S5). For example, the carbon isotope $^{11}C$, which is a short-lived isotope, with a half-life of 20 minutes, is used to produce radiopharmaceuticals and biomarkers for performing a PET examination.

In one embodiment, it is optional, as indicated by the dashed-line arrow, to make a change of the target (S6). In one exemplary embodiment, it is possible to optionally replace the nitrogen target with an oxygen target, so that via the nuclear reaction $^{16}O(p,\alpha)^{13}N$, instead of the carbon isotope, a nitrogen isotope is generated. In this exemplary embodiment, a suitable radiopharmaceutical or biomarker can be produced using the nitrogen isotope. Since the nitrogen isotope $^{13}N$ has a half-life of 10 minutes, the production of the radioactive isotopes and radiopharmaceuticals or biomarkers is suitably completed directly on-site, for example, in a hospital or a clinical device that performs the nuclear medicine examination. In one embodiment, any suitable nuclear reaction may used to produce any suitable radiopharmaceutical or biomarker.

In one embodiment, a second projectile, for example, a deuteron projectile, is accelerated (S3). The linear accelerator that is used is suitable for accelerating a plurality of projectiles. In one embodiment, a second isotope is generated (S4). In one exemplary embodiment, the second isotope is generated using a nuclear reaction $^{20}Ne(d,\alpha)^{18}F$, in which the radioisotope $^{18}F$, with a half-life of 110 minutes, is generated. The first isotope (S2) and the second isotope (S4) are used to produce radiopharmaceuticals and/or biomarkers (S5).

In one embodiment, a lightweight, compact linear accelerator is used. The minimal radiation protection requirements of the linear accelerator allow the linear accelerator to be operated without difficulties, for example, in hospitals, clinics and/or examination devices. In this embodiment, the suitable radiopharmaceuticals and biomarkers are flexibly available as needed.

Figure 2:
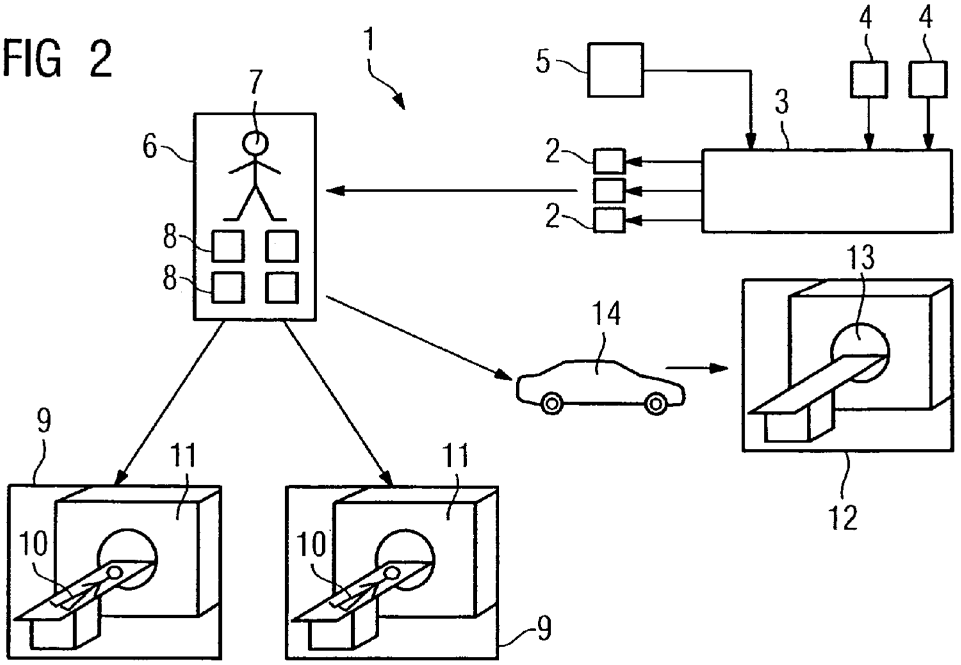
FIG. 2 shows one embodiment of producing and using radioactive isotopes for PET in a clinical device.

In one embodiment shown in FIG. 2, the clinical device 1 includes a linear accelerator 3, which is operated as needed with different projectiles 4. PET examinations may be performed in the clinical device 1. The linear accelerator 3 that serves to produce radioactive isotopes for PET is operated as a function of specifications 5. The specifications 5 include the quantity and type of radioactive isotopes 2 to be generated.

In one embodiment, the linear accelerator 3, which may be operated with the various projectiles 4, generates various radioactive isotopes 2. In one embodiment, as shown in FIG. 2, the radioactive isotopes 2 are processed in a processing device 6 either by, for example, one or more employees 7, automatically, or semiautomatically, to make radiopharmaceuticals and/or biomarkers 8. The radiopharmaceuticals and/or biomarkers 8, depending on the type of projectile 4 or target used, include different radioactive isotopes. The radiopharmaceuticals and/or biomarkers 8 may include radioactive isotopes with longer and/or shorter half-lives, which are each specifically suitable for specific diagnostic examinations.

In one embodiment, the radiopharmaceuticals and/or biomarkers 8, which have thus been generated "on demand", for example, on-site in the clinical device 1, are sent to the examination sites 9. The examination sites 9 include patients 10 that are examined in PET scanners 11. In one embodiment, radiopharmaceuticals and/or biomarkers 8 and the functional imaging of the PET makes early detection of tumors possible.

In one embodiment, any suitable radiopharmaceuticals and/or biomarkers 8 may be produced. For example, radiopharmaceuticals and/or biomarkers 8 may be especially produced for external PET scanners 12, which utilize PET examination devices 13, but that has an incidence of examination that is too low to justify operating a linear accelerator of its own. The transport to the external PET scanner 12 is completed by the transport device 14, for example, an automobile. In one embodiment, the transport is limited to PET scanners 12 in the vicinity of the clinical system 1. In this embodiment, the closeness, in terms of location, of the external PET scanner is better than in previous distribution centers because linear accelerators are more readily available. In this embodiment, a better supply of radioactive isotopes 2, or radiopharmaceuticals and biomarkers 8 may be distributed to the external PET scanner because the transport time is reduced.

In one embodiment, the linear accelerator 3 may be integrated without major effort or expense into clinical devices 1 because of its lightweight, compact construction and substantial avoidance of neutron flows because of the use of a plurality of projectiles. The particular suitable radiopharmaceutical and/or the suitable biomarker 8 is available on demand for performing a specific examination. The particular suitable radiopharmaceutical and/or the suitable biomarker 8 is not limited to one long-lived or short-lived isotope. In one embodiment, a long-lived and/or short-lived isotope may be used.

Figure 3:
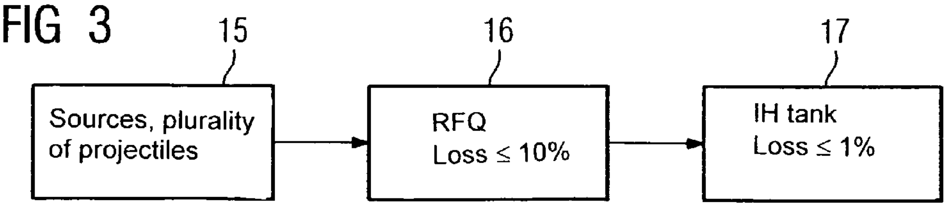
FIG. 3 is a flow chart for the radiation protection in a procedure.

In one embodiment, as shown in FIG. 3, the linear accelerator is operated with a plurality of different projectiles. The source 15, which is operated with a plurality of different projectiles, is adjoined by the RFQ region 16. In the RFQ region, the radiation loss is limited by the upper limit of 10%. This RFQ region is adjoined by the IH tank 17. The IH tank 17 is limited by the upper limit for the radiation loss of 1%. The abbreviations "RFQ" and "IH" stand for "radiofrequency quadrupole" and "interdigital H field", respectively.

In one embodiment, alternatively to the IH tank, in another acceleration resonator operated in the H mode, any suitable tank is provided for example, a CH tank. In this embodiment, the resonator may be operated in the crossbar H mode.

In one embodiment, effective radiation protection is achieved because of the limitations to the losses in the various sections downstream of the source.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for producing radioactive isotopes for positron emission tomography, the method comprising:

generating radioactive isotopes for positron emission tomography by the acceleration of a projectile in a linear accelerator that is operative to accelerate at least two different types of projectiles and generate at least two different corresponding types of radioactive isotopes.

2. The method as defined by claim 1, wherein the projectile comprises protons, deutrons, or both.

3. The method as defined by claim 1, wherein generating radioactive isotopes comprises generating radioactive isotopes with half-lives of over one hour, equal to one hour, less than one hour, or any combination thereof.

4. The method as defined by claim 1, wherein generating the radioactive isotopes, comprises: using nuclear reactions that generate alpha particles.

5. The method as defined by claim 4, wherein generating the radioactive isotopes, comprises: using the nuclear reactions $^{20}Ne(d,\alpha)^{18}F$, $^{14}N(p,\alpha)^{11}C$, $^{16}O(p,\alpha)^{13}N$, or any combination thereof.

6. The method as defined by claim 1, comprising:

generating the radioactive isotopes with the linear accelerator in a hospital or a clinical or diagnostic system; and producing radiopharmaceuticals, biomarkers, or radiopharmaceuticals and biomarkers from the generated radioactive isotopes in the hospital or the clinical or diagnostic system.

7. The method as defined by claim 1, comprising:

changing an amplitude and a phase of the linear accelerator to use a different projectile.

8. The method as defined by claim 2, comprising: attaining projectile energies at a target of the linear accelerator.

9. The method as defined by claim 8, wherein the linear accelerator includes a radiofrequency quadrupole and an acceleration resonator operated in the H mode.

10. The method as defined by claim 3, comprising: generating $^{18}F$, $^{11}C$, $^{13}N$, or any combination thereof.

11. The method as defined by claim 8, comprising: attaining projectile energies for protons in the amount of about 5 MeV to 15 MeV or for deuterons in the amount of about 10 MeV to 20 MeV.

12. The method as defined by claim 8, comprising: attaining projectile energies for protons in the amount of about 5 MeV to 15 MeV and for deuterons in the amount of about 10 MeV to 20 MeV.

13. The method as defined by claim 9, wherein the linear accelerator includes an acceleration resonator operated in the interdigital or the crossbar H mode.

14. The method as defined by claim 13, wherein beam losses in the RFQ amount to 10% or less and the beam losses in the IH tank or the CH tank amount to 1% or less.

15. The method as defined by claim 13, wherein beam losses in the RFQ amount to 10% or less or the beam losses in the IH tank or the CH tank amount to 1% or less.

* * * * *